United States Patent
Hepbildikler et al.

(10) Patent No.: US 9,657,054 B2
(45) Date of Patent: May 23, 2017

(54) IMMUNOGLOBULIN AGGREGATE REMOVAL

(71) Applicant: F. Hoffmann-La Roche AG, Basel (CH)

(72) Inventors: Stefan Hepbildikler, Munich (DE); Wolfgang Kuhne, Penzberg (DE); Eva Rosenberg, Munich (DE); Gerhard Winter, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 398 days.

(21) Appl. No.: 13/651,188

(22) Filed: Oct. 12, 2012

(65) Prior Publication Data

US 2013/0109056 A1 May 2, 2013

Related U.S. Application Data

(63) Continuation of application No. PCT/EP2011/055800, filed on Apr. 13, 2011.

(30) Foreign Application Priority Data

Apr. 14, 2010 (EP) ..................................... 10003968

(51) Int. Cl.
| | | |
|---|---|---|
| *C07K 1/22* | (2006.01) | |
| *C07K 1/18* | (2006.01) | |
| *C07K 19/00* | (2006.01) | |
| *C07K 1/20* | (2006.01) | |
| *C07K 1/32* | (2006.01) | |
| *C07K 16/06* | (2006.01) | |

(52) U.S. Cl.
CPC .................. *C07K 1/22* (2013.01); *C07K 1/20* (2013.01); *C07K 1/32* (2013.01); *C07K 16/065* (2013.01); *C07K 2317/24* (2013.01)

(58) Field of Classification Search
None
See application file for complete search history.

(56) References Cited

U.S. PATENT DOCUMENTS

| 4,606,825 A | 8/1986 | Crane et al. |
| 2002/0010319 A1 | 1/2002 | Ansaldi et al. |
| 2007/0072074 A1 | 3/2007 | Yamamoto et al. |
| 2010/0311952 A1* | 12/2010 | Falkenstein et al. ...... 530/387.1 |

FOREIGN PATENT DOCUMENTS

| DE | 3907162 C2 | 6/1989 |
| JP | 2005/145852 | 6/2005 |
| WO | 2005/044856 A2 | 5/2005 |
| WO | 2008/145351 A1 | 12/2008 |

OTHER PUBLICATIONS

Fringeli, "In situ infrared attunuated total reflection (IR ATR) spectroscopy: a complementary analytical tool for drug design and drug delivery" Chimia 46:200-214 (1992).

Manning J.N. et al., "Reversed-phase liquid chromotography of elastin peptides" Journal of Chromatography 487(1):41-50 (1989).

Mecs et al., "Purification of human leukocyte interferon alpha by carboxymethyl controlled pore glass bead chromatography" Archives of Virology 81:303-311 ( 1984).

Ma et al., "Using precipitation by polyamines as an alternative to chromatopgraphic seperation in antibody purification process" Journal of Chromatography 878:798-806 ( 2010).

Grdadolnik, "An attenuated total reflection infrared sprectoscopy of water solutions" The Internet Journal of Vibrational Spectroscopy 6(2):1-11 ( 2002).

Ghose et al., "Silica and it's application in downstream processing—a blast from the past" Abstracts of Papers, 224th ASC National Meeting, Boston, ( Aug. 18-22, 2002).

Ghose et al., "Preparative protein purification on underivatized silica" Biotechnology and Bioengineering 87(3):413-423 (Aug. 5, 2004).

Mizutani T., "Comparison of elution patterns of proteins chromatographed on controlled-pore glass and carboxymethyl-cellulose" J Chromatogr 168(1):143-150 ( 1979).

Stankovic et al. et al., "Purification of gramicidin A" Anal Biochem 184(1):100-103 ( 1990).

Lifsics et al., "Physicochemical characterization of the 68 000-dalton protein of bovine neurofilaments" Biochemistry 23(13):2866-2875 ( 1984).

Reifsnyder et al. et al., "Purification of Insulin-Like Growth Factor-I and Related Proteins Using Underivatized Silica." J Chromatogr A 753:73-80 ( 1996).

Edy et al. et al., "Purification of interferon by adsorption chromatography on controlled pore glass" J Gen Virol 33(3):517-521 (1976).

Goldberg et al., "Undistorted structural analysis of soluble proteins by attenuated total reflectance infrared spectroscopy" Protein Science 14:2781-2792 ( 2005).

Mizutani, "Adsorption Chromatography of Biopolymers on Porous Glass" Journal of Liquid Chromatography 8(5):925-983 (1985).

(Continued)

*Primary Examiner* — Daniel E Kolker
*Assistant Examiner* — James Rogers

(57) ABSTRACT

For the removal of high molecular weight compounds from recombinantly produced polypeptides generally chromatographic methods are employed. It has been found that underivatized controlled pore glass (uCPG) selectively binds high molecular weight compounds present in a solution. The purified polypeptide can be recovered e.g. from the flow through of a chromatography column containing uCPG as chromatography material. It has been found that this effect is pronounced at a pH value of about 4 to 6 in buffered solutions. With approximately 100 m$^2$ to 150 m$^2$ uCPG surface per g of polypeptide almost 80% to 95% of the high molecular weight compounds are removed with a yield of 80% to 90% of polypeptide.

10 Claims, 8 Drawing Sheets

(56) References Cited

OTHER PUBLICATIONS

Schnabel et al., "Controlled-Pore Glass as a Stationary Phase in Chromatography" Journal of Chromatography 544:137-146 (1991).

* cited by examiner

IMMUNOGLOBULIN AGGREGATE REMOVAL

CROSS-REFERENCE TO RELATED APPLICATIONS

This is a continuation of International Application PCT/EP2011/055800, with an international filing date of Apr. 13, 2011, now abandoned, the entire contents of which are incorporated herein by reference, and which claims priority to European Patent Application No. 10003968.4 filed Apr. 14, 2010.

FIELD OF THE INVENTION

Herein is reported a method for the separation of dimeric and oligomeric immunoglobulin from monomeric immunoglobulin by selective adsorption to underivatized controlled pore glass.

BACKGROUND OF THE INVENTION

Proteins and especially immunoglobulins play an important role in today's medical portfolio. Polypeptides for use in pharmaceutical applications are mainly produced in mammalian cells such as CHO cells, NS0 cells, Sp2/0 cells, COS cells, HEK cells, BHK cells, PER.C6® cells, and the like.

Due to their chemical and physical properties, such as molecular weight and domain architecture including secondary modifications, the downstream processing of immunoglobulins is very complicated. For example, are not only for formulated drugs but also for intermediates in downstream processing (DSP) concentrated solutions required to achieve low volumes for economic handling and application storage. The down stream processing of biotechnologically produced immunoglobulins in general comprises three chromatography steps: a first affinity chromatography step using e.g. Protein A, to remove non-immunoglobulin molecules, normally followed by two ion exchange chromatography steps, whereof the last step is a so called polishing step to remove DNA and HCP contaminants. The purified immunoglobulin is obtained in a low concentration solution requiring a concentration step prior to formulating the antibody into the pharmaceutical formulation. Due to the non-natural conditions required during the down stream processing the normally monomeric immunoglobulin tends to form dimers, oligomer and higher order aggregates. These aggregates do not possess the intended antigen-binding activity of the monomeric immunoglobulin and have to be removed. Ghose, S., et al. (Biotechnol. Bioeng. 87 (2004) 413-423) report preparative protein purification on underivatized silica. Reifsnyder, D. H., et al. (J. Chrom. A 753 (1996) 73-80) report the capture of IGF-I from a crude fermentation broth and a specific elution using a combination of ethanol and NaCl. Lifsics, M. R. and Williams, R. C. Jr (Biochem. 23 (1984) 2866-2875) report a molecular sieve chromatography in 8 M urea on controlled-pore glass for separating monomeric and aggregated forms of a protein from bovine neurofilaments. Ghose, S., et al. (Abstracts of Papers, 224th ACS National Meeting, Boston, Mass., United States, Aug. 18-22, 2002 (2002), BIOT-317 Publisher: American Chemical Society, Washington, D.C.) report the use of underivatized naked silica gel as a preparative stationary phase for process purification of proteins.

In U.S. Pat. No. 4,606,825 a method of separating and recovering immunoglobulin G using controlled pore glass bearing non-cross-linked covalently bound polyethylene imine functions is reported. A method for separating a polypeptide monomer from a mixture comprising dimers and/or multimers using an ion exchange chromatography resin and a gradient elution is reported in US 2002/0010319. Mizutani, T. and Mizutani, A., J. Chrom. 168 (1979) 143-150 report the comparison of elution patterns of proteins chromatographed on controlled-pore glass and carboxymethyl cellulose. The isolation and purification of the enzyme myeloperoxidase using a chromatography with carboxymethylated controlled pore glass is reported in DE 39 07 162 A1.

SUMMARY OF THE INVENTION

It has been found that underivatized controlled pore glass (uCPG) surfaces selectively bind dimeric and oligomeric, i.e. aggregated, immunoglobulin of class G (IgG) present in a solution at a pH value of from pH 5 to pH 7.5. By applying of from 50 $m^2$ to 150 $m^2$ uCPG surface per gram of total IgG, up to 95% of the soluble aggregates are bound to the particles (as determined by SE-HPLC). Concomitantly, only about 10% to 20% of the monomer is adsorbed to the surface. This can be achieved simply by batch-wise adding the uCPG to the solution comprising monomer and aggregates and thereafter removing the uCPG with the bound aggregates by centrifugation or filtration. Incubation of the protein over 6 days with uCPG did not result in the formation of aggregates. Moreover, no detectable changes to protein secondary or tertiary structure could be observed after the incubation with uCPG.

Thus, an aspect as reported herein is a method for obtaining a polypeptide in monomeric form or aggregated form wherein the method comprises the following steps
  a) providing a solution comprising the polypeptide in monomeric form and in aggregated form,
  b) incubating the solution with underivatized controlled pore glass at a pH value of from pH 4 to pH 6, and
  c) recovering the polypeptide from the incubated solution and thereby obtaining the polypeptide in monomeric form,
or the following steps
  a) providing a solution comprising the polypeptide in monomeric form and in aggregated form,
  b) incubating the solution with underivatized controlled pore glass at a pH value of from pH 4 to pH 6,
  c) removing the controlled pore glass from the solution,
  d) incubating the removed controlled pore glass with a solution of a pH value of from pH 2 to pH 3 or of from pH 7 to pH 8 and thereby obtaining the polypeptide in aggregated form.

Another aspect as reported herein is a method for producing a polypeptide comprising
  a) providing a eukaryotic cell comprising a nucleic acid encoding the polypeptide,
  b) cultivating the cell to express the polypeptide,
  c) recovering the polypeptide from the cells or the cultivation medium,
  d) incubating a solution comprising the recovered polypeptide with underivatized controlled pore glass at a pH value of from pH 4 to pH 6, and
  e) recovering the polypeptide from the incubated solution and thereby producing the polypeptide.

In one embodiment the underivatized controlled pore glass is underivatized controlled pore glass beads. In a further embodiment underivatized controlled pore glass with a surface of 100 $m^2$ to 150 $m^2$ per gram of polypeptide is used. In another embodiment the polypeptide is an immunoglobulin, or an immunoglobulin fragment, or an immunoglobulin conjugate. In also an embodiment the pH value is adjusted by a buffer solution of the respective pH value. In a further embodiment the method is a batch method. In also an embodiment the solution comprises a discrete amount of polypeptide and the solution is incubated with a discrete amount of underivatized controlled pore glass. In also an embodiment the solution is a buffered solution. In one embodiment the recovering is by centrifugation or filtration. In a further embodiment the incubating is for 1 minute to 6 hours.

In one embodiment all the methods may comprise as last step the step of purifying the polypeptide by one or more chromatographic separation steps.

Also an aspect as reported herein is the use of underivatized controlled pore glass for the adsorption of high molecular weight polypeptides at a pH value of from pH 4 to pH 6.

A further aspect as reported herein is a kit of parts comprising a) underivatized controlled pore glass beads,
b) a buffered solution of a pH value of from pH 4 to pH 6,
c) a buffered solution of a pH value of from pH 2 to pH 3,
d) a buffered solution of a pH value of from pH 7 to pH 8.

DETAILED DESCRIPTION OF THE INVENTION

Figure 1:
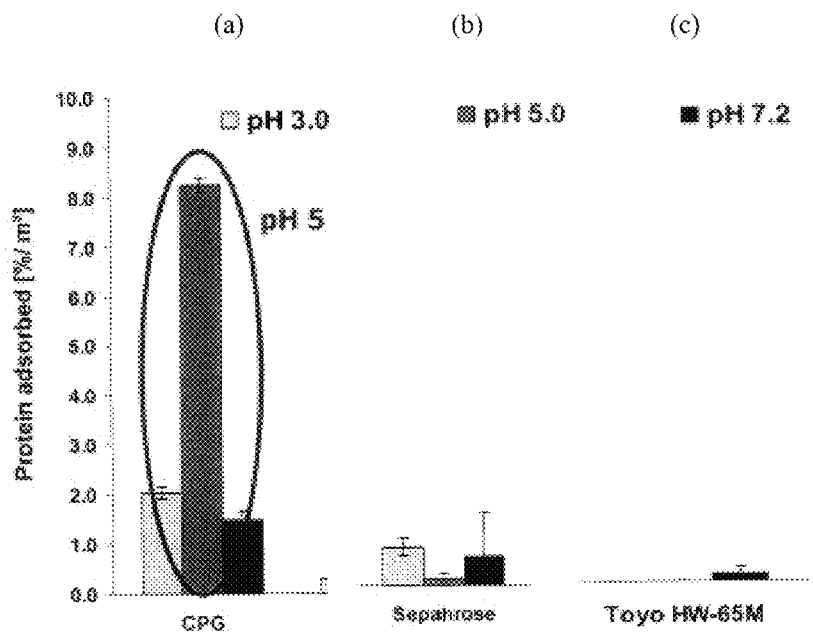
FIG. 1 A: Comparison of the adsorption properties of underivatized controlled pore glass (a), crosslinked agarose (Sepharose) (b) and poly (methacrylate) (c) at pH values of 3.0, 5.0 and 7.2. B: Adsorption of IgG to CPG matrices at pH 3, pH 5, pH 7.5 Percent protein adsorbed per square meter bead surface referring to the protein mass initially present before incubation; adsorption at pH 3.0 (light grey), at pH 5.0 (dark grey) and at pH 7.5 (black); results are presented as mean values of three measurements±SD.
Figure 1:
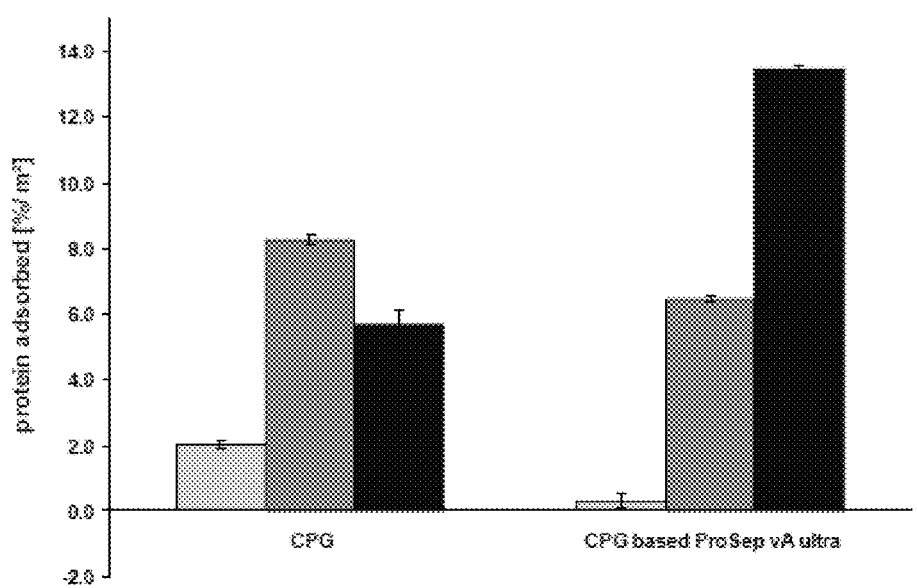

Generally, for the separation of monomeric immunoglobulin from aggregated immunoglobulin as well as other high molecular weight compounds commonly chromatographic methods are employed. It has now been found that underivatized controlled pore glass (uCPG) selectively binds dimeric and oligomeric immunoglobulins and high molecular weight compounds present in solution e.g. compared to underivatized Sepharose™. The monomeric immunoglobulin can be recovered e.g. from the flow through of a chromatography column containing uCPG as chromatography material or from the supernatant of an incubation of a solution with uCPG. This effect is pronounced at a pH value of about 5.0 in buffered solutions. With approximately 50 $m^2$ to 150 $m^2$ uCPG surface per g of immunoglobulin up to 95% of the aggregated form can be removed with a yield of 80% to 90% of monomeric immunoglobulin.

The application of uCPG can be used to remove dimers and oligomers from active pharmaceutical ingredient bulks or final formulated material prior to or even after storage.

A "polypeptide" is a polymer of amino acid residues joined by peptide bonds, whether produced naturally or synthetically. Polypeptides of less than about 20 amino acid residues are referred to as "peptides". A "protein" is a macromolecule comprising one or more polypeptide chains or at least one polypeptide chain of more than 100 amino acid residues. A polypeptide may also comprise non-peptidic components, such as carbohydrate groups. Carbohydrate groups and other non-peptidic substituents may be added to a polypeptide by the cell in which the polypeptide is produced, and will vary with the type of cell. Polypeptides are defined herein in terms of their amino acid backbone structures; substituents such as carbohydrate groups are generally not specified, but may be present nonetheless.

The term "immunoglobulin" refers to a protein comprising one or more polypeptide(s) substantially encoded by immunoglobulin genes. The recognized immunoglobulin genes include the different constant region genes as well as the immunoglobulin variable region genes. Immunoglobulins may exist in a variety of formats, including, for example, Fv, Fab, and F(ab)$_2$ as well as single chains (scFv) or diabodies.

The term "complete immunoglobulin" denotes an immunoglobulin which comprises two light immunoglobulin chain polypeptides (light chains) and two heavy immunoglobulin chain polypeptides (heavy chains). Each of the heavy and light immunoglobulin chain polypeptides contains a variable domain (variable region, generally the amino terminal portion) comprising binding regions that are able to interact with an antigen. Each of the heavy and light immunoglobulin chain polypeptides comprises a constant region (generally the carboxyl terminal portion). The variable domain of an immunoglobulin light or heavy chain in turn comprises different segments, i.e. four framework regions (FR) and three hypervariable regions (CDR).

The term "immunoglobulin fragment" denotes a polypeptide comprising at least one domain selected from the variable domain ($V_H$), the $C_H1$ domain, the hinge-region, the $C_H2$ domain, the $C_H3$ domain, or the $C_H4$ domain of a heavy chain, or the variable domain ($V_L$) or the $C_L$ domain of a light chain. Also enclosed are derivatives and variants thereof. For example, a variable domain, in which one or more amino acids or amino acid regions are deleted, may be present.

The term "immunoglobulin conjugate" denotes a polypeptide comprising at least one domain of an immunoglobulin heavy or light chain conjugated via a peptide bond to a further polypeptide. The further polypeptide can be a non-immunoglobulin peptide, such as a hormone, or toxin, or growth receptor, or antifusogenic peptide, or complement factor, or the like.

For the purification of recombinantly produced immunoglobulins a combination of different column chromatography steps can be employed. Generally a protein A affinity chromatography is followed by one or two additional separation steps. The final purification step is a so called "polishing step" for the removal of trace impurities and contaminants like aggregated immunoglobulins, residual HCP (host cell protein), DNA (host cell nucleic acid), viruses, or endotoxins. For this polishing step an anion exchange material in flow-through mode can be used.

Different methods can be used for protein recovery and purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis).

The terms "immunoglobulin in monomeric form" and "monomeric immunoglobulin", which can be used interchangeably, as well as grammatical equivalents thereof denote an immunoglobulin molecule that is not associated with a second immunoglobulin molecule, i.e. which is neither covalently nor non-covalently bound to another immunoglobulin molecule. The terms "immunoglobulin in aggregated form" and "aggregated immunoglobulin", which can be used interchangeably, and "dimeric immunoglobulin" and "multimeric immunoglobulin" as well as grammatical equivalents of all denote an immunoglobulin molecule which is associated, either covalently or non-covalently, with at least one additional immunoglobulin molecule, and which is eluted in a single peak from a size exclusion chromatography column. The term "in monomeric form" and grammatical equivalents thereof as used within this application not necessarily denotes that 100% of an immunoglobulin molecule are present in monomeric form. It denotes that an immunoglobulin is essentially in monomeric form, i.e. at least 90% of the immunoglobulin is in monomeric from, in one embodiment at least 95% of the immunoglobulin is in monomeric form, in another embodiment at least 98% of the immunoglobulin is in monomeric form, in a further embodiment at least 99% of the immunoglobulin is in monomeric form, and in a final embodiment more than 99% of the immunoglobulin is in monomeric form determined as peak area of a size exclusion chromatogram. The term "in monomeric and in aggregated form" denotes a mixture of immunoglobulin molecules not associated with other immunoglobulin molecules and of immunoglobulin molecules associated with other immunoglobulin molecules. In this mixture neither of the monomeric form nor the aggregated form is present exclusively. The term "high molecular weight (HMW) form" denotes polymeric, i.e. aggregated, immunoglobulin, whereby said aggregate is still soluble in an aqueous buffered solution.

The term "100%" as used within this application denotes that the amount of components other than a specified component is below the detection limit of the referred to analytical method under the specified conditions.

The terms "90%", "95%", "98%", "99%" as used within this application denote no exact values but values within the accuracy of the referred to analytical method under the specified conditions.

A chromatographic material comprises a core material and thereto attached chromatographic functional groups. The core material can be an inorganic material, such as silica, zeolithe, hydroxyapatite, or glass, an organic material, such as cellulose, or agarose, or a synthetic polymeric material, such as poly (methacrylate).

The solutions employed in the method as reported herein are in one embodiment buffered solutions. The term "buffered solution" denotes a solution in which changes of pH due to the addition or release of acidic or alkaline substances is leveled by the dissolved buffer substance. Any buffer substance with such properties can be used. Generally pharmaceutically acceptable buffers substances are used. In one embodiment the buffered solution is selected from a phosphate buffered solution consisting of phosphoric acid and/or salts thereof, or an acetate buffered solution consisting of acetic acid and/or salts thereof, or a citrate buffered solution consisting of citric acid and/or salts thereof, or a morpholine buffered solution, or a 2-(N-morpholino) ethanesulfonic buffered solution, or a histidine buffered solution, or a glycine buffered solution, or a tris (hydroxymethyl) aminomethane (TRIS) buffered solution. In another embodiment the buffered solution is selected from a phosphate buffered solution, or an acetate buffered solution, or a citrate buffered solution, or a histidine buffered solution. Optionally the buffered solution may comprise an additional salt, such as e.g. sodium chloride, sodium sulphate, potassium chloride, potassium sulfate, sodium citrate, or potassium citrate.

Underivatized chromatographic core materials, especially underivatized controlled pore glass, can be used to selectively adsorb polypeptides, especially immunoglobulins in aggregated form, i.e. dimeric and oligomeric immunoglobulin molecules.

Generally, CPG beads have a mean particle diameter of about 125 μm. The specific surface area of the herein used CPG beads was determined to be 36 $m^2$/g.

In FIG. 1A the adsorption properties of underivatized controlled pore glass, crosslinked agarose (Sepharose™) and poly (methacrylate) are shown. It can be seen that polypeptides can bind to underivatized controlled pore glass on the one hand and on the other hand that a strong pH dependency of the binding capacity can be seen. As can be seen in FIG. 1B the ProSep vA ultra medium shows the highest adsorption of the IgG at pH 7.5. ProSep vA ultra is a functionalized CPG material in which a Protein A affinity ligand is coupled to the glass surface. At a pH of 5.0 adsorption of IgG to CPG was observed to be higher than to the functionalized Protein A gel.

Figure 2:
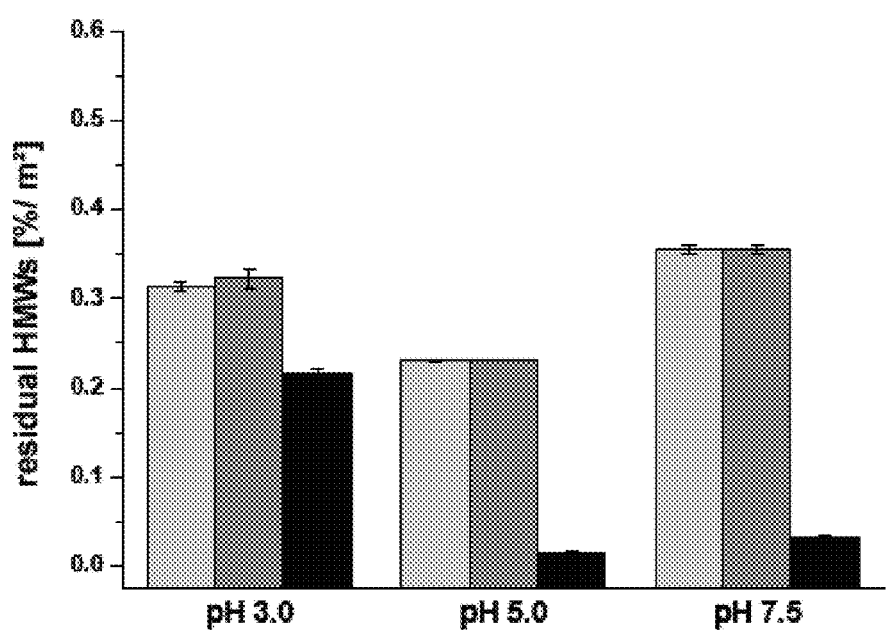
FIG. 2 Residual HMWs per square meter CPG surface; percent HMWs determined with SE-HPLC in the supernatant referring to the amount of HMWs initially present before incubation with the surface; before incubation (light grey), incubation without chromatographic surface (dark grey), and incubated with chromatographic surface (black); results are presented as mean values of three measurements±SD.

After incubation of the IgG with uCPG at different pH values of pH 3.0, 5.0 and 7.5 the supernatant was analyzed by SE-HPLC. It was observed, that after incubation with underivatized CPG beads at pH 5.0 and 7.5, the solution was almost fully cleared from soluble aggregates (FIG. 2).

Figure 6:
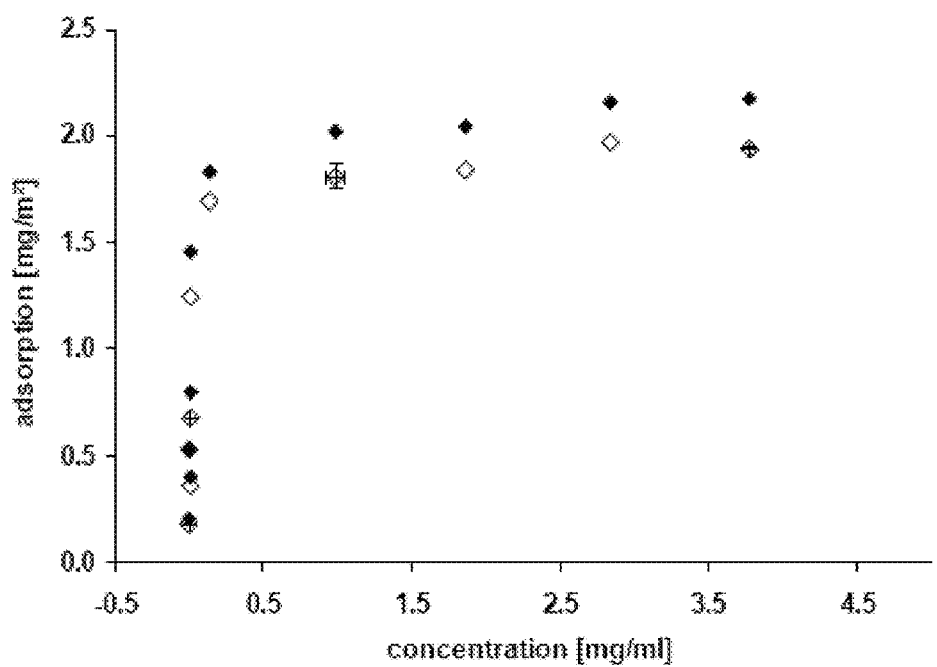
FIG. 6 Adsorption and desorption isotherm of IgG on CPG particles; adsorption (black diamonds) studies were done at pH 5.0, desorption (plain diamonds) at pH 3.0; results are presented as mean values of three measurements±SD.

FIG. 6 shows the amount of IgG adsorbed to uCPG after 12 hour incubation at a pH value of pH 5.0 versus the concentration of protein in the supernatant. Saturation can be reached at relatively low protein concentrations and maximum adsorption can be reached at 2.0 mg IgG per square meter CPG. Quantitative desorption can be effected when the protein loaded CPG is incubated in a buffered solution at a pH value of pH 3.0. Adsorption of protein to silica surfaces is in general reported to be reversible under defined conditions. Harsh chemical solvents like chloroform, methanol, or 2-propanol can be used (see e.g. Manning, J. N., et al., Journal of Chromatography B 487 (1989) 41-50; Stankovic, C. J., et al., Anal. Biochem. 184 (1990) 100-103). Moreover chaotropic salts can be used (see e.g. Mecs, I., et al., Arch. Virol. 81 (1984) 303-311) besides a changing of the pH value (see e.g. Edy, V. G., et al., J. Gen. Virol. 33 (1976) 517-521).

Figure 7:
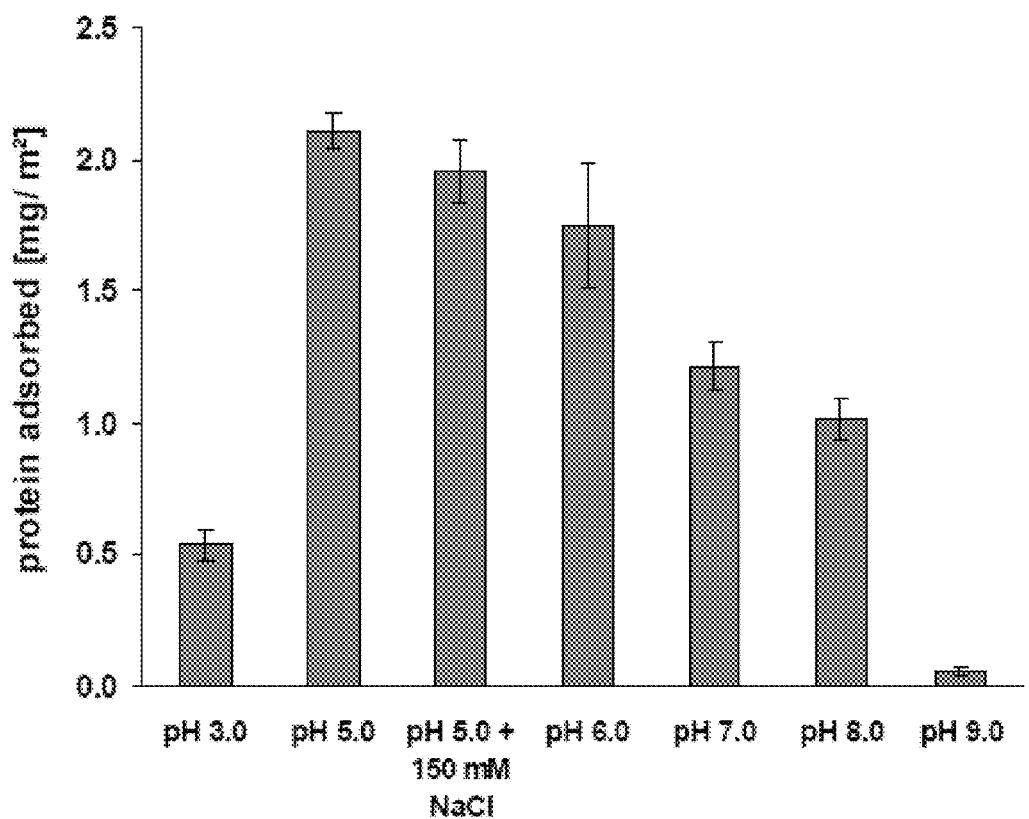
FIG. 7 Adsorption of IgG on CPG particles at different pHs; experiments were carried out in the saturation regime at a soluble protein concentration of 2 mg/ml or higher; results are presented as mean values of three measurements±SD.
Figure 8:
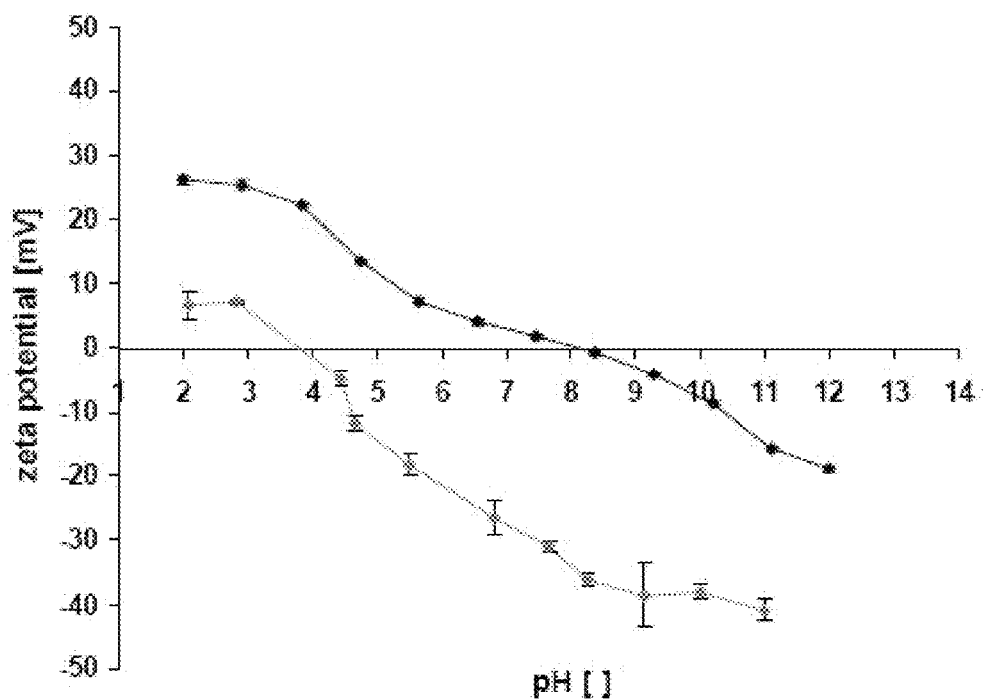
FIG. 8 Zeta potential titration curves of the IgG (black) and the nano-sized CPG particles (grey); experimental data is presented as mean values of three measurements±SD.

Maximum adsorption can be observed at pH 5.0 (FIG. 7). A decrease in IgG adsorption can be observed when the pH is raised above the isoelectric point (IP) of the IgG (e.g. the IP was determined to be 8.0 by using zeta potential measurements for the IgG shown in FIG. 8). The zeta-potential of the IgG can be determined depending on a pH value titration.

The surface charge of the nano-sized CPG depends on the pH value as well. The IP of the CPG can be determined to be about 4. At a pH value above pH 4 the surface charge of the CPG changes from positive to negative.

Figure 4:
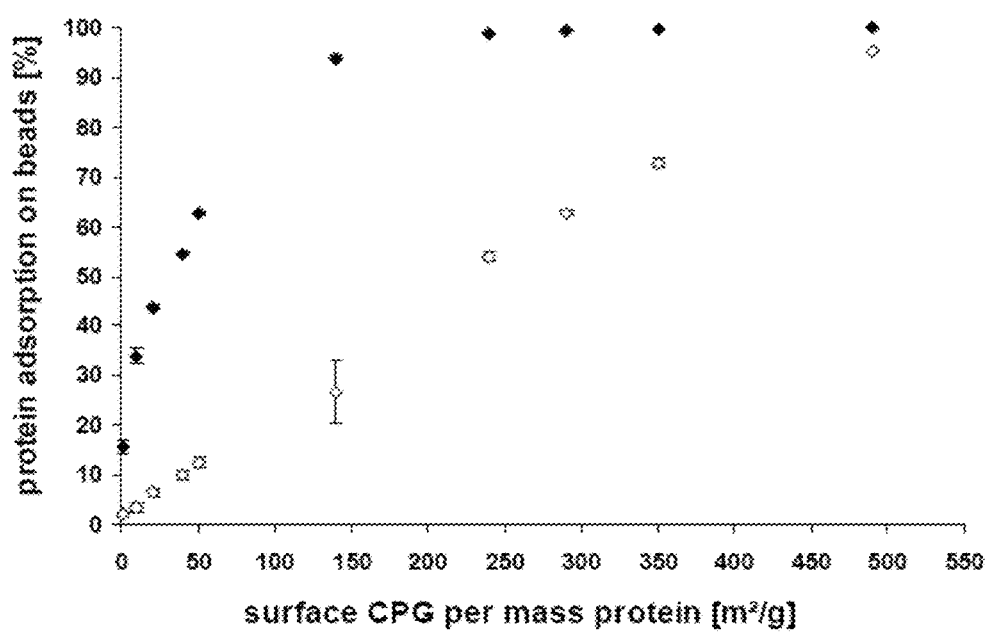
FIG. 4 Adsorption of IgG monomer (plain) and HMWs (black) on CPG; 20 mg IgG containing 6.8% HMWs were initially present before incubation with 0.1-10 $m^2$ CPG; experimental data is presented as mean values of three measurements±SD.

For example, a solution containing 6.8% of HMWs was incubated with different uCPG surface areas of 0.1 $m^2$ to 10 $m^2$ at a pH value of about 5. The residual percentage of HMWs (high molecular weight compounds) in solution was determined in the supernatant using SE-HPLC. In FIG. 4 the amount of monomer and HMWs in percent adsorbed to the CPG surface area per gram protein, which was initially present before incubation, is shown. When 50 $m^2$ CPG surface per gram IgG is employed, 63% of the HMWs initially present in the solution can be adsorbed. Nine percent of the monomer initially present in the solution is bound to the particles. By applying about 140 $m^2$ CPG surface per gram protein, nearly 95% of HMWs can be bound, while only 22% of monomer is adsorbed. At about 250 $m^2$ CPG surface per gram protein almost 100% of the HMWs can be adsorbed on the CPG surface (see FIG. 5). Between 50 $m^2$ and 150 $m^2$ CPG surface per gram protein, the oligomers can be removed almost completely. The CPG surface area present during incubation has no effect on the amount of the LMWs (low molecular weight compounds) remaining in solution.

Thus, soluble aggregates of immunoglobulins can be adsorbed to underivatized CPG. The surface area of CPG available per gram protein can be used to control the amount of aggregated and monomeric species remaining in solution after incubation. A surface area between 100 $m^2$ to 150 $m^2$ per gram protein can be used to remove 60% to 95% of soluble aggregates from an IgG solution at a pH value of about 5, having concomitantly 80% to 90% monomeric IgG remaining in solution.

The conformation of the protein was investigated before, during and after adsorption to the surface. No protein loss due to the formation of insoluble aggregates can be observed during six day incubation. The level of HMWs determined by SE-HPLC decreased with increasing CPG surface area. After an incubation of one day no further decrease in the level of soluble aggregates can be detected if the incubation is prolonged for 5 days. No increase of HMWs in the supernatant can be determined. In one embodiment the incubation is for 1 min. to 24 hours. In a further embodiment the incubation is for 1 min. to 6 hours.

The exposure of IgG to uCPG did not result in conformational alterations of the secondary structure as determined with FT-IR spectroscopy.

An aspect as reported herein is a method for obtaining a polypeptide comprising the step
   incubating the polypeptide with underivatized controlled pore glass at a pH value of from pH 4 to pH 6.

In one embodiment the underivatized controlled pore glass is used at a pH value of from pH 4.5 to pH 5.5. In another embodiment the uCPG is used at a pH value of about pH 5. In another embodiment the incubating is in a buffered solution.

The term "about" denotes that the thereafter following value is no exact value but is the center point of a range that is in one embodiment +/−10% of the value, or in another embodiment +/−5% of the value, or in a further embodiment +/−2% of the value, or in an embodiment +/−1% of the value. If the value is a relative value given in percentages the term "about" also denotes that the thereafter following value is no exact value but is the center point of a range that is in one embodiment +/−10% of the value, or in another embodiment +/−5% of the value, or in a further embodiment +/−2% of the value, or in an embodiment +/−1% of the value, whereby the upper limit of the range cannot exceed a value of 100%.

In one embodiment the method for obtaining a polypeptide, especially an immunoglobulin, in monomeric form comprises the following steps
   a) incubating a solution comprising the polypeptide in monomeric form and in aggregated form with underivatized controlled pore glass at a pH value of from pH 4 to pH 6,
   b) recovering the supernatant and thereby obtaining the polypeptide in monomeric form from the supernatant of step a).

In another embodiment the method for obtaining a polypeptide, especially an immunoglobulin, in aggregated form comprises the flowing steps
   a) incubating a solution comprising the polypeptide in monomeric form and in aggregated form with underivatized controlled pore glass at a pH value of from pH 4 to pH 6,
   b) recovering the incubated underivatized controlled pore glass,
   c) recovering the polypeptide in aggregated form from the underivatized controlled pore glass by incubation with a solution with a pH value differing by at least two pH units from the pH value of the solution of step a).

In one embodiment the incubation is by adding a defined amount of underivatized controlled pore glass to the solution comprising the polypeptide. In also an embodiment the incubating is by applying the solution to a chromatography column comprising the underivatized controlled pore glass. In the first embodiment the polypeptide is recovered from the supernatant of the incubation. In the second embodiment the polypeptide is recovered from the flow-through of the column. The recovering of the high molecular weight compounds is in both embodiments by applying a solution with a pH value differing by at least two pH units from the pH value of the incubation solution to the controlled pore glass. In one embodiment the first method is a batch method.

In one embodiment the method comprises the following steps
  purifying a solution comprising the immunoglobulin with a Protein A affinity chromatography,
  optionally purifying the immunoglobulin with an ion exchange chromatography,
  incubating the obtained immunoglobulin comprising solution with underivatized controlled pore glass at a pH value of from pH 4 to pH 6,
  recovering the supernatant of the previous step and thereby obtaining the immunoglobulin in monomeric form.

Another aspect as reported herein is a method for producing a polypeptide, especially an immunoglobulin, in monomeric form comprising
  a) cultivating a cell comprising a nucleic acid encoding the polypeptide,
  b) recovering the polypeptide from the cell or the cultivation medium,
  c) incubating the polypeptide with underivatized controlled pore glass at a pH value of from pH 4 to pH 6,
  d) recovering the supernatant of step c) and thereby producing the polypeptide in monomeric form.

In one embodiment the incubating with the underivatized controlled pore glass is for 1 min. to 120 min.

Figure 3:
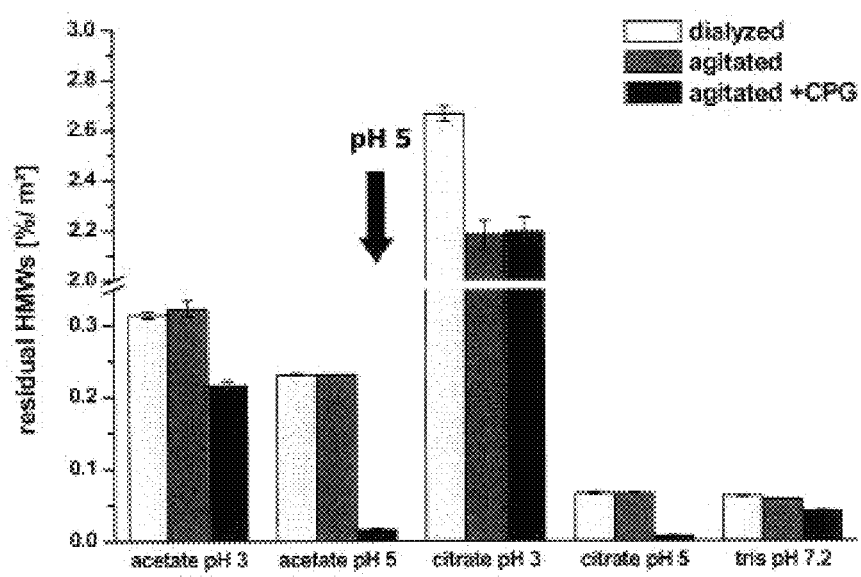
FIG. 3 Comparison of the specific accumulation of high molecular weight (HMW) compounds on underivatized controlled pore glass depending on the pH value and the buffer compound.

In FIG. 3 the accumulation of high molecular weight (HMW) compounds on underivatized controlled pore glass depending on the pH value and the buffer compound is shown. It can be seen that underivatized controlled pore glass at a pH value of approximately pH 5 adsorbs high molecular weight compounds from an immunoglobulin solution independent of the buffer substance. In one embodiment the buffer substance is selected from acetic acid or a salt thereof, such as sodium or potassium acetate, and citric acid or a salt thereof, such as sodium or potassium citrate.

In FIG. 4 the adsorption of high molecular weight (HMW) compounds on underivatized controlled pore glass is compared to the adsorption of monomeric immunoglobulin. It can be seen that the adsorbed amount of HMW compounds shows an exponential dependency on the surface area of controlled pore glass per mass of applied polypeptide. The adsorbed amount of monomeric immunoglobulin shows a linear dependency on the surface of controlled pore glass per mass of applied polypeptide.

Figure 5:
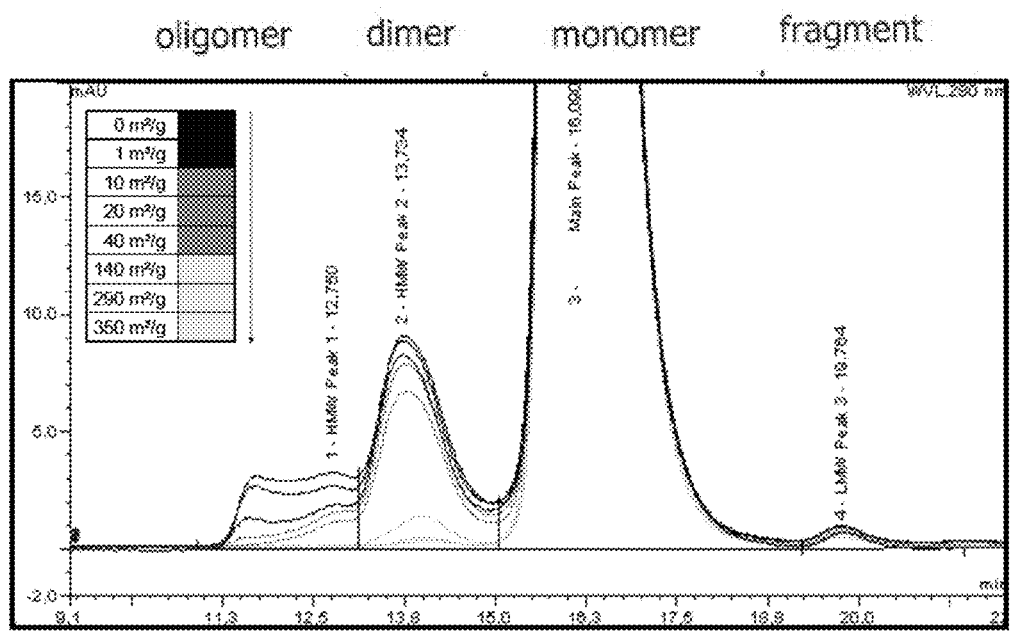
FIG. 5 SE-chromatograms of the IgG solutions after incubation with up to 350 $m^2$ surface area of CPG per gram protein; 20 mg IgG containing 6.8% HMWs were initially present before incubation with CPG (black profile); decreasing UV-signal with increasing CPG surface is indicated by changing the color from black to light grey.

In FIG. 5 a size exclusion chromatogram of differently treated solutions is shown. It can be seen that e.g. the use of 140 m$^2$ CPG surface per gram of polypeptide results in a reduction of high molecular weight compounds.

In FIG. 6 the surface coverage of underivatized controlled pore glass is shown. It can be seen that the surface coverage reached 2 mg/m$^2$ surface of underivatized controlled pore glass. The adsorption is reversible by changing the pH value. In one embodiment the adsorbed high molecular weight compounds are recovered from the underivatized controlled pore glass by changing the pH value from pH 5 to a value differing by at least two pH units, in one embodiment to pH 3.0 or to pH 7.0.

By 2$^{nd}$ derivative UV- or IR-spectroscopy it can be shown that the adsorption does not affect the secondary or tertiary structure.

Due to the selective adsorption of high molecular weight compounds from immunoglobulin preparations the use of underivatized controlled pore glass can be suitable for the purification of active pharmaceutical ingredients at the end of the down stream processing in order to remove remaining immunoglobulin in aggregated form. The operating pH value of from pH 5 to pH 6 corresponds to the pH value of bulk active pharmaceutical ingredients. With underivatized controlled pore glass it is possible to remove oligomeric and even dimeric immunoglobulin forms which is otherwise difficult at late stages in down stream processing. Additionally a handling in batch mode can be made by simply incubating underivatized controlled pore glass beads with the bulk protein solution and removing aggregates with the removal of the CPG e.g. by centrifugation or filtration.

The following examples and figures are provided to aid the understanding of the present invention, the true scope of which is set forth in the appended claims. It is understood that modifications can be made in the procedures set forth without departing from the spirit of the invention.

Example 1

Materials and Methods

Antibody

A completely purified bulk of a chimeric human Fc (IgG1)/rat Fab antibody in histidine buffer pH 6.0 (IgG A) was taken for the experiments. Aliquots were dialyzed into 100 mM acetate buffer pH 3.0, 100 mM acetate buffer pH 5.0 and 200 mM tris (hydroxymethyl)-aminomethane buffer pH 7.5. The solutions were filtrated afterwards by using a Sterivex-GV 0.22 µm filter (Millipore, Billerica, USA).

CPG

Controlled pored glass (CPG 700) beads from Millipore (Billerica, USA) were used.

Chemicals

All other chemicals and reagents used were at least analytical grade. Acidic acid was taken from Fluka (Steinheim, Germany), citric acid, hydrochloric acid, sodium hydroxide and sodium chloride were taken from Merck KG (Darmstadt, Germany), tris (hydroxymethyl)-aminomethan was taken from Angus (Ibbenbueren, Germany). L-histidine from Ajinomoto (Raleigh, USA) was used.

Adsorption to Surfaces

Adsorption of the monoclonal antibody (mAb) to CPG surface was investigated at different pHs by incubating a defined surface with a defined protein mass. Therefore, the bead slurry was suspended and mixed with purified water (Milli-Q, Millipore, Billerica, USA). The beads were collected by vacuum filtration (0.22 µm cellulose filter discs, Sartorius, Goettingen, Germany) and afterwards rinsed with purified water (Milli-Q, Millipore, Billerica, USA). Subsequently, the beads were dried at 40° C. and a defined mass was weighed representing a defined surface as determined by gas adsorption (BET). Afterwards, the beads were mixed with the protein solution at a defined pH and incubated without head space on the rotary mixer RM5 (Froebel, Lindau, Germany) at 35 rpm for 12 hours at room temperature. The samples were then centrifuged for 10 min. at 10,000×g to separate the beads from the protein solution. Protein concentration determination and SE-HPLC analysis were performed with the supernatant of the centrifuged samples. Triplicate samples were prepared and the results are presented as mean values±SD.

Adsorption isotherms of mAb on different bead surfaces were determined by preparing samples containing 5 m$^2$ bead surface and various concentrations of mAb between 0.2 mg/ml and 6.0 mg/ml. The samples were incubated over 12 hours as described before and were centrifuged for 10 min. at 10,000×g to separate the beads from the protein solution and to determine the protein concentration in the supernatant. The amount of protein adsorbed was determined by subtracting the amount of the protein determined in the supernatant from the amount of protein initially present before incubation. Triplicate samples were prepared and the results are presented as mean values±SD.

To look at preferential adsorption of HMWs on CPG surfaces the IgG in 100 mM acetate buffer pH 5 containing 6.8% HMWs was incubated with 0.1-10 $m^2$ CPG surface. The samples were incubated for 12 hours as described before and were centrifuged for 10 min. at 10,000×g to separate the beads from the protein solution and to determine the protein concentration in the supernatant. In addition, the supernatant was analyzed by SE-HPLC. The amount of adsorbed HMWs and monomer respectively was determined by subtracting the amount of HMWs determined in the supernatant from the amount of HMWs initially present before incubation. Triplicate samples were prepared and the results are presented as mean values±SD.

Protein Concentration Determination

Protein concentration was determined by using the photometric absorbance at 280 nm and 320 nm after buffer blank subtraction (UV-Vis spectrophotometer Evolution 500, Thermo Fisher Scientific, Waltham, USA). The absorbance at 320 nm was subtracted from the absorbance at 280 nm and this absorbance value was used to calculate the protein content according to the law of Lambert-Beer.

SE-HPLC

Size exclusion high pressure liquid chromatography (SE-HPLC) experiments were conducted with a TSK 3000 SWXL column (Tosoh Bioseparation, Stuttgart, Germany) on a Summit HPLC-system (Dionex, Idstein, Germany). The elution peaks were monitored at 280 nm by the UV diode array detector UVD170U from Dionex (Idstein, Germany). Isocratic chromatography was conducted at room temperature using an aqueous buffer composed of 200 mM potassium phosphate and 250 mM potassium chloride at pH 7.0 and a flow rate of 0.5 ml/min. Each sample contained 100 µg mAb load per injection. The chromatograms were integrated manually by using the Chromeleon software (Dionex, Idstein, Germany). Percentage of higher molecular weight species (HMWs) including dimers and larger soluble oligomers was determined as relative area (mAU*min) referred to total area including the monomer peak and the peak of lower molecular weight species (LMWs).

FT-IR Spectroscopy

FT-IR spectra were recorded with the Tensor 27 (Bruker Optics, Ettlingen, Germany) applying the MIRacle attenuated total reflection (ATR) cell with a Germanium crystal to investigate the secondary structure of the protein on the bead surface. The CPG beads were incubated at room temperature for 12 hours with a 6 mg/ml solution of IgG in acetate buffer at pH 5.0. The solutions showed a level of 1.5% HMWs determined by SE-HPLC before incubation. Incubation was conducted in saturation mode. After incubation the beads were washed with buffer. The AquaSpec transmission cell was used to investigate the protein secondary structure after desorption from the beads by using a 200 mM tris buffer pH 9.0. For each spectrum which was recorded from 850-4000 $cm^{-1}$ a 120-scan interferogram was collected at a double sided acquisition mode with a resolution of 4 $cm^{-1}$. The reference spectrum of buffer and wetted beads respectively was subtracted to obtain the protein spectrum. The spectra were edited by a vector normalization followed by the generation of the second derivative and smoothing using a 13-point Savitsky-Golay smoothing function applying the OPUS 6.0 software (Bruker Optics, Ettlingen, Germany). Moreover, the absorption spectra recorded in ATR mode were corrected concerning band intensity and band position to allow the comparison to spectra recorded in transmission mode. Therefore, the extended ATR-correction of the software OPUS 6.0 (Bruker Optics, Ettlingen, Germany) according to Fringeli was used (Fringeli, U. P., Chimia 46 (1992) 200-214) to overcome wave number dependent anomalous dispersion (Goldberg, M. E., and Chaffotte, A. F., Protein Sci. 14 (2005) 2781-2792; Grdadolnik, J., Int. J. Vibr. Spec. 6, ed. 2 (2002).

Zeta Potential Measurements

To determine the charge of the protein and the sonicated nano-sized CPG 700 at different pH values, electrophoretic mobility of the protein and the CPG 700 beads was determined by performing Laser-Doppler-Velocimetry using the Malvern Zetasizer Nano S (Malvern Instruments, Worcestershire, UK). The zeta potential ζ was calculated from the Henry's equation with assumption of uniform charge distribution by using the Malvern DTS software (Version 5.0, Malvern Instruments, Worcestershire, UK). For sample preparation a 5 mg/ml mAb solution was dialyzed into 50 mM acetate buffer pH 5.0 and titrated to a pH of 2.0 afterwards by using 0.2 M hydrochloric acid. The CPG 700 beads were suspended in the same buffer system and the pH was adjusted to 2.0. The samples were titrated with a 0.2 M sodium hydroxide solution from pH 2 to pH 12 by applying the titrator MPT2 (Malvern Instruments, Worcestershire, UK). The zeta potential was determined in 15 steps between pH 2 and 12 in a temperature controlled folded capillary cell (Malvern Instruments, Worcestershire, UK) at 25° C. Each measurement was repeated threefold and mean values±SD are reported.

The invention claimed is:

1. A method for obtaining an immunoglobulin in monomeric form, characterized in that the method comprises the following steps:
    a) incubating a solution comprising the polypeptide in monomeric form and in aggregated form with underivatized controlled pore glass with a surface of 100 $m^2$ to 150 $m^2$ per gram of immunoglobulin at a pH value of from pH 4.5 to pH 5.5, wherein the incubating is by applying the solution to a chromatography column comprising the "underivatized"controlled pore glass, and
    b) recovering a flow-through and thereby obtaining the immunoglobulin in monomeric form.

2. A method for producing a immunoglobulin comprising:
    a) cultivating a eukaryotic cell comprising a nucleic acid encoding the immunoglobulin,
    b) recovering the immunoglobulin from the cell or the cultivation medium,
    c) incubating a solution comprising the recovered immunoglobulin with an underivatized controlled pore glass with a surface of 100 $m^2$ to 150 $m^2$ per gram of immunoglobulin at a pH value of from pH 4.5 to pH 5.5, and
    d) recovering a supernatant and thereby producing the immunoglobulin, wherein the incubating is by applying the solution to a chromatography column comprising the underivatized controlled pore glass, and wherein the recovering is from the flow-through of the column.

3. The method according to claim 1, characterized in that the underivatized controlled pore glass are underivatized controlled pore glass beads.

4. The method according to claim 2, characterized in that the underivatized controlled pore glass are underivatized controlled pore glass beads.

5. The method according to claim 1, characterized in that the solution is a buffered Solution of the respective pH value.

6. The method according to claim 2, characterized in that the solution is a buffered solution of the respective pH value.

7. The method according to claim 1, characterized in comprising as last step (c)the step of
(c)purifying the immunoglobulin by one more chromatographic separation steps.

8. The method according to claim 2, characterized in comprising as last step (e) the step of
(e) purifying the immunoglobulin by one or more chromatographic separation steps.

9. The method according to claim 1, characterized in that the incubating is for 1 minute to 6 hours.

10. The method according to claim 2, characterized in that the incubating is for 1 minute to 6 hours.

\* \* \* \* \*